United States Patent
Baker, Jr. et al.

(10) Patent No.: US 6,461,353 B1
(45) Date of Patent: *Oct. 8, 2002

(54) ORTHOPEDIC APPARATUS FOR CONTROLLED CONTRACTION OF COLLAGEN TISSUE

(75) Inventors: James A. Baker, Jr., Palo Alto; Edward J. Gough, Menlo Park, both of CA (US)

(73) Assignee: Oratec Interventions, Inc., Menlo Park, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/888,359

(22) Filed: Jul. 3, 1997

Related U.S. Application Data

(63) Continuation of application No. 08/390,873, filed on Feb. 17, 1995, now abandoned.

(51) Int. Cl.$^7$ .......................... A61B 18/14; A61B 18/18
(52) U.S. Cl. .......................... 606/41; 606/42; 607/100; 607/101; 607/102
(58) Field of Search ........................ 606/27, 28, 32–52; 600/151, 100; 604/154, 158, 168; 607/100–103

(56) References Cited

U.S. PATENT DOCUMENTS

| | | |
|---|---|---|
| 2,090,923 A | 8/1937 | Wappler |
| 3,178,728 A | 4/1965 | Christensen |

(List continued on next page.)

FOREIGN PATENT DOCUMENTS

| | | |
|---|---|---|
| DE | 3511107 A1 | 10/1986 |
| DE | 3632197 A1 | 3/1988 |

(List continued on next page.)

OTHER PUBLICATIONS

Sluijter et al., Persistent Pain, Modern Methods of Treatment, "Treatment of Chronic Back and Neck Pain by Percutaneous Thermal Lesions", vol. 3 (1981), pp. 141–179.

(List continued on next page.)

*Primary Examiner*—David M. Shay
(74) *Attorney, Agent, or Firm*—Fish & Richardson P.C.

(57) ABSTRACT

An orthopedic apparatus, for effecting a change in ligaments, joint capsules and connective tissue through the controlled contraction of collagen fibers, includes a trocar. The trocar has a trocar elongated body with a trocar longitudinal axis, a trocar distal end that is laterally deflectable relative to the trocar longitudinal axis, and a trocar proximal end. An electrode is positioned at the trocar distal end. The electrode delivers substantially uniform energy across an energy delivery surface of the electrode. The energy delivery surface is positioned next to an area of collagen fibers to cause a controlled amount of contraction of the collagen fibers while minimizing dissociation and breakdown of the collagen fibers. A handle is positioned at the proximal end of the trocar. The handle includes an actuating member and a locking member. The actuating member has a resting position and one or more activation positions that cause the trocar distal end to become laterally deflected to a desired position of deflection. The locking member has a resting position and a locking position that locks the deflected trocar distal end in place. Further, the locking member is releasable from the locking position to the resting position or to one that is intermediate between the two in order to modify the activation position of the actuating member and change the deflection of the trocar distal end. The distal end's deflection can be readily adjusted and can return to a non-deflected position. The handle can be held in one hand, and the actuating and locking members each operable by a thumb and a finger of the hand.

18 Claims, 5 Drawing Sheets

U.S. PATENT DOCUMENTS

| | | |
|---|---|---|
| 3,579,643 A | 5/1971 | Morgan |
| 3,776,230 A | 12/1973 | Neefe |
| 3,856,015 A | 12/1974 | Iglesias |
| 3,867,728 A | 2/1975 | Substad et al. |
| 3,879,767 A | 4/1975 | Substad |
| 3,886,600 A | 6/1975 | Kahn et al. |
| 3,938,198 A | 2/1976 | Kahn et al. |
| 3,945,375 A | 3/1976 | Banko |
| 3,987,499 A | 10/1976 | Scharbach et al. |
| 3,992,725 A | 11/1976 | Homsy |
| 4,043,342 A | 8/1977 | Morrison, Jr. |
| 4,074,718 A | 2/1978 | Morrison |
| 4,085,466 A | 4/1978 | Goodfellow et al. |
| 4,129,470 A | 12/1978 | Homsy |
| 4,134,406 A | 1/1979 | Iglesias |
| 4,224,696 A | 9/1980 | Murray et al. |
| 4,224,697 A | 9/1980 | Murray et al. |
| 4,326,529 A | 4/1982 | Doss et al. |
| 4,344,193 A | 8/1982 | Kenny |
| 4,362,160 A | 12/1982 | Hiltebrandt |
| 4,375,220 A | 3/1983 | Matvias |
| 4,381,007 A | 4/1983 | Doss |
| 4,397,314 A | 8/1983 | Vaguine |
| 4,476,862 A | 10/1984 | Pao |
| 4,483,338 A | 11/1984 | Bloom et al. |
| 4,517,965 A | 5/1985 | Ellison |
| 4,517,975 A | 5/1985 | Garito et al. |
| 4,590,934 A | 5/1986 | Malis et al. |
| 4,593,691 A | 6/1986 | Lindstrom et al. |
| 4,597,379 A | 7/1986 | Kihn et al. |
| 4,601,705 A | 7/1986 | McCoy |
| 4,651,734 A | 3/1987 | Doss et al. |
| 4,811,733 A | 3/1989 | Borsanyi et al. |
| 4,815,462 A | 3/1989 | Clark |
| 4,838,859 A | 6/1989 | Strassmann |
| 4,846,175 A | 7/1989 | Frimberger |
| 4,873,976 A | 10/1989 | Schreiber |
| 4,894,063 A | 1/1990 | Nashef |
| 4,895,148 A | 1/1990 | Bays et al. |
| 4,907,585 A | 3/1990 | Schachar |
| 4,907,589 A | 3/1990 | Cosman |
| 4,924,865 A | 5/1990 | Bays et al. |
| 4,944,727 A * | 7/1990 | McCoy ............... 600/151 |
| 4,950,234 A | 8/1990 | Fujioka et al. |
| 4,955,882 A | 9/1990 | Hakky |
| 4,966,597 A | 10/1990 | Cosman |
| 4,976,709 A | 12/1990 | Sand |
| 4,976,715 A | 12/1990 | Bays et al. |
| 4,998,933 A | 3/1991 | Eggers et al. |
| 5,007,908 A | 4/1991 | Rydall |
| 5,009,656 A | 4/1991 | Reimels |
| 5,085,657 A | 2/1992 | Ben-Simhon |
| 5,085,659 A | 2/1992 | Rydell |
| 5,098,430 A | 3/1992 | Fleenor |
| 5,100,402 A | 3/1992 | Fan |
| 5,103,804 A | 4/1992 | Abele et al. |
| 5,114,402 A | 5/1992 | McCoy |
| 5,152,748 A | 10/1992 | Chastagner |
| 5,178,620 A | 1/1993 | Eggers et al. |
| 5,186,181 A | 2/1993 | Franconi et al. |
| 5,191,883 A | 3/1993 | Lennox et al. |
| 5,192,267 A | 3/1993 | Shapira et al. |
| 5,201,729 A | 4/1993 | Hertzmann et al. |
| 5,201,730 A | 4/1993 | Easley et al. |
| 5,201,731 A | 4/1993 | Hakky |
| 5,213,097 A | 5/1993 | Zeindler |
| 5,230,334 A | 7/1993 | Klopotek |
| 5,242,439 A | 9/1993 | Larsen et al. |
| 5,242,441 A | 9/1993 | Avitall |
| 5,261,906 A | 11/1993 | Pennino et al. |
| 5,267,994 A | 12/1993 | Gentelia et al. |
| 5,273,535 A * | 12/1993 | Edwards et al. ............ 128/772 |
| 5,275,151 A | 1/1994 | Shockey et al. |
| 5,279,559 A | 1/1994 | Barr |
| 5,284,479 A | 2/1994 | de Jong |
| 5,304,169 A | 4/1994 | Sand |
| 5,308,311 A | 5/1994 | Eggers et al. |
| 5,311,858 A * | 5/1994 | Adair ..................... 600/106 |
| 5,320,115 A | 6/1994 | Kenna |
| 5,323,778 A | 6/1994 | Kandarpa et al. |
| 5,334,193 A | 8/1994 | Nardella |
| 5,342,357 A | 8/1994 | Nardella |
| 5,348,554 A | 9/1994 | Imran et al. |
| 5,352,868 A | 10/1994 | Denen et al. |
| 5,354,331 A | 10/1994 | Schachar |
| 5,364,395 A | 11/1994 | West, Jr. |
| 5,366,443 A | 11/1994 | Eggers et al. |
| 5,366,490 A | 11/1994 | Edwards et al. |
| 5,382,247 A | 1/1995 | Cimino et al. |
| 5,397,304 A | 3/1995 | Truckai |
| 5,401,272 A | 3/1995 | Perkins |
| 5,415,633 A | 5/1995 | Lazarus et al. |
| 5,423,806 A | 6/1995 | Dale et al. |
| 5,433,739 A | 7/1995 | Sluijter et al. |
| 5,437,661 A | 8/1995 | Rieser |
| 5,437,662 A | 8/1995 | Nardella |
| 5,451,223 A | 9/1995 | Ben-Simhon |
| 5,458,596 A * | 10/1995 | Lox et al. ................ 606/31 |
| 5,464,023 A | 11/1995 | Viera |
| 5,465,737 A | 11/1995 | Schachar |
| 5,484,403 A | 1/1996 | Yoakum et al. |
| 5,484,432 A | 1/1996 | Sand |
| 5,484,435 A | 1/1996 | Fleenor et al. |
| 5,487,757 A | 1/1996 | Truckai et al. |
| 5,498,258 A | 3/1996 | Hakky et al. |
| 5,500,012 A | 3/1996 | Brucker et al. |
| 5,507,812 A | 4/1996 | Moore |
| 5,514,130 A | 5/1996 | Baker |
| 5,524,338 A | 6/1996 | Martyniuk et al. |
| 5,527,331 A | 6/1996 | Kresch et al. |
| 5,542,920 A | 8/1996 | Cherif Cheikh |
| 5,569,242 A | 10/1996 | Lax et al. |
| 5,599,356 A | 2/1997 | Edwards et al. |
| 5,630,839 A | 5/1997 | Corbett, III et al. |
| 5,681,282 A | 10/1997 | Eggers et al. |
| 5,683,366 A | 11/1997 | Eggers et al. |
| 5,688,270 A | 11/1997 | Yates et al. |
| 5,697,909 A | 12/1997 | Eggers et al. |
| 5,718,702 A | 2/1998 | Edwards |
| 5,782,795 A | 7/1998 | Bays |
| 5,810,809 A | 9/1998 | Rydell |

FOREIGN PATENT DOCUMENTS

| | | | |
|---|---|---|---|
| DE | 39 18316 | | 3/1990 |
| EP | 0 257 116 A1 | | 3/1988 |
| EP | 0 274 705 A1 | | 7/1988 |
| EP | 0 479 482 A1 | | 4/1992 |
| EP | 0 572 131 A1 | | 1/1993 |
| EP | 0 542 412 A1 | | 5/1993 |
| EP | 0 521 595 A2 | | 7/1993 |
| EP | 0 558 297 A2 | | 9/1993 |
| EP | 0 566 450 A1 | | 10/1993 |
| EP | 0 682 910 A1 | | 11/1995 |
| EP | 0 479 482 B1 | | 5/1996 |
| EP | 0 729 730 A1 | | 9/1996 |
| EP | 0 737 487 A2 | | 10/1996 |
| EP | 0 783 903 A1 | | 7/1997 |
| FR | 1122634 | | 9/1956 |
| FR | 2 645 008 | | 10/1990 |
| GB | 1 340 451 | | 12/1973 |
| GB | 637118 | | 12/1978 |
| GB | 2 164 473 A | | 3/1986 |
| JP | 5-42166 | | 5/1993 |
| WO | WO 82/02488 | | 8/1982 |
| WO | 8502762 | * | 7/1983 ............ 606/50 |
| WO | WO 92/05828 | | 4/1992 |

| | | |
|---|---|---|
| WO | WO 92/10142 | 6/1992 |
| WO | WO 93/01774 | 4/1993 |
| WO | WO 93/16648 | 9/1993 |
| WO | WO 93/20984 | 10/1993 |
| WO | WO 95/01814 | 1/1995 |
| WO | WO 95/20360 | 3/1995 |
| WO | WO 95/10981 | 4/1995 |
| WO | WO 95/13113 | 5/1995 |
| WO | WO 95/18575 | 7/1995 |
| WO | WO 95/25471 | 9/1995 |
| WO | WO 95/30377 | 11/1995 |
| WO | WO 95/34259 | 12/1995 |
| WO | WO 96/11638 | 4/1996 |
| WO | WO 96/32051 | 10/1996 |
| WO | WO 96/32885 | 10/1996 |
| WO | WO 96/34559 | 11/1996 |
| WO | WO 96/34568 A | 11/1996 |
| WO | WO 96/34571 | 11/1996 |
| WO | WO 96/39914 | 12/1996 |
| WO | WO 97/06855 | 2/1997 |
| WO | WO 98/07468 | 2/1998 |
| WO | WO 98/17190 | 4/1998 |

OTHER PUBLICATIONS

PRNewswire ( Dec. 12, 1994), "Two Physicians Perform First Outpatient Cervical Disc Procedure Using Laser Technology".

Introduction to the LDD Disc Kit, Oct. 16, 1996, one page—photograph obliterated.

Mayer et al., "Lasers in Percutaneous Disc Surgery: Beneficial Technology or Gimmick?", *Acta Orthop. Scand.*, Suppl. 251 (1993) pp. 38–44.

Savitz M. A., "Same–day Microsurgical Arthroscopic Lateral–approach Laser–assisted (SMALL) Fluoroscopic Discectomy", *J. Neurosurg.*, vol. 80, Jun. 1994 pp. 1039–1045.

Bosacco et al., "Functional Results of Percutaneous Laser Discectomy", *American Journal of Orthopedics*, Dec. 1996, pp. 825–828.

Leu et al., "Endoskopie der Wirbelsaule: Minimal–invasive Therapie", *Der Orthopade*, vol. 21, (1992) pp. 267–272 no translation.

Cosman et al., "Theoretical Aspects of Radiofrequency Lesions in the Dorsal Root Entry Zone", *Neurosurgery*, vol. 15, No. 6 (1984) pp. 945–950.

Gottlob et al., "Holmium:YAG Laser Ablation of Human Intervertebral Disc: Preliminary Evaluation", *Lasers in Surgery and Medicine*, vol. 12, (1992) pp. 86–91, no translation.

Buchelt et al., "Fluorescence Guided Excimer Laser Ablation of Intervertebral Discs In Vitro", *Lasers in Surgery and Medicine*, vol. 11, (1991) pp. 280–286.

Choy et al., "Percutaneous Laser Disc Decompression: A New Therapeutic Modality", *SPINE*, vol. 17, No. 8, (1992) pp. 949–956.

Sluijter, M., "The use of radio frequency lesions for pain relief in failed back patients", *Int. Disabil. Studies*, vol. 10, (1988) pp. 37–43.

Shatz et al., "Preliminary Experience With Percutaneous Laser Disc Decompression in the Treatment of Sciatica", *CJS JCC*, vol. 38, No. 5, Oct. 1995 pp. 432–436.

Gerber et al., "Offene Laserchirurgie am Bewegungsapparat", *Der Orthopade*, vol. 25, (1996) pp. 56–63 only summary translated.

Kelly L.E., Purification and Properties of a 23kDa $Ca^{2+}$–binding Protein from *Drosophila melanogaster, Biochem. J.*, vol. 271 (1990), pp. 661–666.

Sluyter, M., "Radiofrequency Lesions in the Treatment of Cervical Pain Syndromes", Technical series publication, Radionics, Inc. (1989), pp. 2–25.

Buchelt et al., "Erb:YAG and Hol:YAG Laser Ablation of Meniscus and Intervertebral Discs", *Lasers in Surgery and Medicine*, vol. 12, No. 4, (1992) pp. 375–381.

Phillips et al., "MR Imaging of Ho: YAG Laser Diskectomy with Histologic Correlation", *JMRI*, vol. 3, No. 3, May/Jun. 1993, pp. 515–520.

Bromm et al., "Nerve fibre discharges, cerebral potentials and sensations induced by $CO_2$ laser stimulation", *Human Neurobiol.*, vol. 3, (1984) pp. 33–40.

Kolarik et al., Photonucleolysis of intervertebral disc and its herniation, *Zent. bl. Neurochir.*, vol. 51, (1990) pp. 69–71.

Vorwerck et al., "Laserablation des Nucleus pulposus: Optische Eigenschaften von Degeneriertem Bandscheibengewebe im Wellenlangenbereich von 200 bis 2200nm", *Fortschr. Roentgenstr.*, vol. 151, No. 6, (1989) pp. 725–728 no translation.

Wolgin et al., "Excimer Ablation of Human Intervertebral Disc at 308 Nanometers", *Lasers in Surgery and Medicine*, vol. 9, (1989) pp. 124–131.

Davis, "Early Experience with Laser Disc Decompression", *J. Florida M. A.*, vol. 79, No. 1 (1992), pp. 38–39.

Quigley et al., "Laser Discectomy: Comparison of Systems", *SPINE*, vol. 19, No. 3 (1994) pp. 319–322.

Mehta et al., "The treatment of chronic back pain: A preliminary survey of the effect of radiofrequency denervation of the posterior vertebral joints", *Anaesthesia*, vol. 34 (1979) pp. 768–775.

Patil et al., "Percutaneous Discectomy Using the Electomagnetc Field Focusing Probe: A Feasibility Study", *Int. Surg.*, vol. 76 (1991), pp. 30–32.

McCulloch et al., Percutaneous radiofrequency lumbar rhizolysis (rhizotomy), *CMA Journal*, vol. 116, Jan. 8, 1977, pp. 30–32.

Yonezawa et al., "The System and Procedures of Percutaneous Intradiscal Laser Nucleotomy", *SPINE*, vol. 15, No. 11 (1990), p. 1175–1185.

Sminia et al., "Effects of 434 MHz microwave hyperthermia applied to the rat in the region of the cervical spinal cord", *Int. J. Hyperthermia*, vol. 3, No. 5 (1987) pp. 441–452.

Auhll, Richard A., "The Use of the Resectoscope in Gynecology." Biomedical Business International, Oct. 11, 1990, pp. 91–93.

Christian, C. et al., "Allograft Anterior Cruciate Ligament Reconstruction with Patellar Tendon: An Endoscopic Technique", *Operative Techniques in Sports Medicine*, vol. 1, No. 1, Jan. 1993, pp. 50–57.

Houpt, J. et al., "Experimental Study of Temperature Distributions and Thermal Transport During Radiofrequency Current Therapy of the Intervertebral Disc", *SPINE*, vol. 21, No. 15, (1996), pp. 1808–1813.

Troussier, B. et al., "Percutaneous Intradiscal Radio–Frequency Thermocoagulation: A Cadaveric Study", *SPINE*, vol. 20, No. 15, (Aug. 1995), pp. 1713–1718.

Beadling, L., "Bi–Polar electrosurgical devices: Sculpting the future of arthroscopy", *Orthopedics today*, vol. 17, No. 1, Jan. 1997, 4 pages.

Ellman International Mfg., Inc., 1989, Catalog, pp. 1–12, 15 20 and order forms.

Cosset, J.M., Resistive Radiofrequency (Low Frequency) Interstitial Heating (RF Technique), Interstitial Hyperthermia, Dec. 6, 1993, pp. 3–5, 37.

* cited by examiner

ORTHOPEDIC APPARATUS FOR CONTROLLED CONTRACTION OF COLLAGEN TISSUE

This application is a continuation, of application Ser. No. 08/390,873, filed Feb. 17, 1995 abandoned.

BACKGROUND OF THE INVENTION

1. Field of the Invention

This invention relates generally to an orthopedic apparatus that delivers a controlled amount of energy to an orthopedic site to contract collagen tissue, and more particularly, to an orthopedic apparatus that includes a handle with an actuating lever to deflect a distal end of a trocar, a locking lever to lock the position of a deflected distal end, wherein the deflection, locking, release and modification of the deflection are all achieved with a handle and the deflection and locking is achieved with a thumb and a finger of the same hand.

2. Description of Related Art

Instability of peripheral joints has long been recognized as a significant cause of disability and functional limitation in patients who are active in their daily activities, work or sports. Diarthrodial joints of musculoskeletal system have varying degrees of intrinsic stability based on joint geometry and ligament and soft tissue investment. Diarthrodial joints are comprised of the articulation of the ends of bones and their covering of hyaline cartilage surrounded by a soft tissue joint capsule that maintains the constant contact of the cartilage surfaces. This joint capsule also maintains within the joint the synovial fluid that provides nutrition and lubrication of the joint surfaces. Ligaments are soft tissue condensations in or around the joint capsule that reinforce and hold the joint together while also controlling and restricting various movements of the joints. The ligaments, joint capsule, and connective tissue are largely comprised of collagen.

When a joint becomes unstable, its soft tissue or bony structures allow for excessive motion of the joint surfaces relative to each other and in directions not normally permitted by the ligaments or capsule. When one surface of a joint slides out of position relative to the other surface, but some contact remains, subluxation occurs. When one surface of the joint completely disengages and loses contact with the opposing surface, a dislocation occurs. Typically, the more motion a joint normally demonstrates, the more inherently loose the soft tissue investment is surrounding the joint. This makes some joints more prone to instability than others. The shoulder, (glenohumeral) joint, for example, has the greatest range of motion of all peripheral joints. It has long been recognized as having the highest subluxation and dislocation rate because of its inherent laxity relative to more constrained "ball and socket" joints such as the hip.

Instability of the shoulder can occur congenitally, developmentally, or traumatically and often becomes recurrent, necessitating surgical repair. In fact subluxations and dislocations are a common occurrence and cause for a large number of orthopedic procedures each year. Symptoms include pain, instability, weakness, and limitation of function. If the instability is severe and recurrent, functional incapacity and arthritis may result. Surgical attempts are directed toward tightening the soft tissue restraints that have become pathologically loose. These procedures are typically performed through open surgical approaches that often require hospitalization and prolonged rehabilitation programs.

More recently, endoscopic (arthroscopic) techniques for achieving these same goals have been explored with variable success. Endoscopic techniques have the advantage of being performed through smaller incisions and therefore are usually less painful, performed on an outpatient basis, are associated with less blood loss and lower risk of infection and have a more cosmetically acceptable scar. Recovery is often faster postoperatively than using open techniques. However, it is often more technically demanding to advance and tighten capsule or ligamentous tissue arthroscopically because of the difficult access to pathologically loose tissue and because it is very hard to determine how much tightening or advancement of the lax tissue is clinically necessary. In addition, fixation of advanced or tightened soft tissue is more difficult arthroscopically than through open surgical methods.

Collagen connective tissue is ubiquitous in the human body and demonstrates several unique characteristics not found in other tissues. It provides the cohesiveness of the musculoskeletal system, the structural integrity of the viscera as well as the elasticity of integument. These are basically five types of collagen molecules with Type I being most common in bone, tendon, skin and other connective tissues, and Type III is common in muscular and elastic tissues.

Intermolecular cross links provide collagen connective tissue with unique physical properties of high tensile strength and substantial elasticity. A previously recognized property of collagen is hydrothermal shrinkage of collagen fibers when elevated in temperature. This unique molecular response to temperature elevation is the result of rupture of the collagen stabilizing cross links and immediate contraction of the collagen fibers to about one-third of their original lineal distention. Additionally, the caliber of the individual fibers increases greatly, over four fold, without changing the structural integrity of the connection tissue.

There has been discussion in the existing literature regarding alteration of collagen connective tissue in different parts of the body. One known technique for effective use of this knowledge of the properties of collagen is through the use of infrared laser energy to effect tissue heating. The use of infrared laser energy as a corneal collagen shrinking tool of the eye has been described and relates to laser keratoplasty, as set forth in U.S. Pat. No. 4,976,709. The importance controlling the localization, timing and intensity of laser energy delivery is recognized as paramount in providing the desired soft tissue shrinkage effects without creating excessive damage to the surrounding non-target tissues.

Radiofrequency (RF) electrical current has been used to reshape the cornea. Such shaping has been reported by Doss in U.S. Pat. Nos. 4,326,529; and 4,381,007. However, Doss was not concerned with dissociating collagen tissue in his reshaping of the cornea.

Shrinkage of collagen tissue is important in many applications. One such application is the shoulder capsule. The capsule of the shoulder consists of a synovial lining and three well defined layers of collagen. The fibers of the inner and outer layers extend in a coronal access from the glenoid to the humerus. The middle layer of the collagen extends in a sagittal direction, crossing the fibers of the other two layers. The relative thickness and degree of intermingling of collagen fibers of the three layers vary with different portions of the capsule. The ligamentous components of the capsule are represented by abrupt thickenings of the inner layer with a significant increase in well organized coarse collagen bundles in the coronal plane.

The capsule functions as a hammock-like sling to support the humeral head. In pathologic states of recurrent traumatic or developmental instability this capsule or pouch becomes attenuated and the capsule capacity increases secondary to capsule redundance. In cases of congenital or developmental multi-directional laxity, an altered ratio of type I to type III collagen fibers may be noted. In these shoulder capsules a higher ratio of more elastic type III collagen has been described.

There is a need for an orthopedic apparatus for effecting a change in ligaments, joint capsules and connective tissue through the controlled contraction of collagen fibers. There is a need for an apparatus that includes a handle with a lateral deflection actuating member that is pulled and causes a distal end of the trocar to be deflected to a desired position, and a locking member on the handle which locks the distal end in a laterally deflected position, and is releasable to modify the amount of deflection of the deflected distal end.

SUMMARY OF THE INVENTION

Accordingly, an object of the invention is to provide an orthopedic apparatus that effects a change in ligaments, joint capsules and connective tissue through the controlled contraction of collagen fibers.

Another object of the invention is to provide an orthopedic apparatus, using an RF or microwave electrode, to effect a change in ligaments, joint capsules and connective tissue through the controlled contraction of collagen fibers.

A further object of the invention is to provide an orthopedic apparatus for the controlled contraction of collagen tissue that includes a trocar with a deflectable distal end, an RF or microwave electrode positioned at the distal end, and a handle that includes a actuating member to deflect the distal end and a locking member to lock the distal end in position. Deflection of the distal end and modification of the amount of deflection is achieved by a single hand.

Yet another object of the invention is to provide an orthopedic apparatus for the controlled contraction of collagen tissue that enables the surgeon to deflect a distal end of a trocar with an electrode surface, lock the deflection, modify the deflection, and permit the trocar to spring back to a non-deflected position with a thumb and a finger of only one hand.

Still a further object of the invention is to provide an orthopedic apparatus for the controlled contraction of collagen tissue that includes a handle which permits the physician to introduce a trocar of the orthopedic apparatus into a desired location of the body, and provide variable deflection of the distal end of the trocar in order to position the distal end at a desired located, and thereafter continue to modify the deflection in order to paint across selected collagen tissue surfaces to achieve a desired contraction of collagen tissue.

Yet another object of the invention is to provide an orthopedic apparatus, for the controlled contraction of collagen tissue, that includes a deflectable trocar distal end and a handle, with the handle permitting a quick modification of deflection, and easy return to a non-deflected position.

These and other objects of the invention are obtained in an orthopedic apparatus for effecting a change in ligaments, joint capsules and connective tissue through the controlled contraction of collagen fibers. A trocar includes a trocar elongated body with a trocar longitudinal axis, a trocar distal end that is laterally deflectable relative to the trocar longitudinal axis, and a trocar proximal end. An electrode is positioned at the trocar distal end. The electrode delivers substantially uniform energy across an energy delivery surface of the electrode. The energy delivery surface positioned next to an area of collagen fibers delivers a controlled amount of contraction of the collagen fibers while minimizing dissociation and breakdown of the collagen fibers. A handle is positioned at the proximal end of the trocar. The handle includes an actuating member and a locking member. The actuating member has a resting position and one or more activation positions. At the activation positions the trocar distal end becomes laterally deflected to a desired position of deflection. The locking member has a resting position and a locking position. The locking position locks the deflected trocar distal end in place. Further, the locking member is releasable from the locking position to the resting position or to a position that is intermediate between the two in order to modify the activation position of the actuating member and change the deflection of the trocar distal end. The distal end's deflection can be readily adjusted and can also return to a non-deflected position. The handle can be held in one hand, and the actuating and locking members are each operable by a thumb and a finger of the hand.

The electrode can be an RF electrode, and the orthopedic apparatus can further include an RF energy source, and a cable that connects the RF energy source to the handle and the electrode.

Further, the electrode be a microwave electrode, and the orthopedic apparatus can include a microwave energy source, and a cable that connects the microwave energy source to the handle and the electrode.

The electrode preferably has radiused edges. An insulating layer is positioned around an exterior of the trocar but does not cover the energy delivery surface of the electrode. A non-conductive layer can also be included and positioned on an opposite side of the electrode. This provides an electrode with only one conductive surface and with radiused edges. The trocar is deflectable. Deflection can be achieved by serrating the trocar, making it out of a memory metal, as well as other methods well known to those skilled in the art. Both the locking and actuating members are coupled to the trocar. The actuating member can be pivotally coupled to the handle, while the locking member can be slideably positioned on a exterior surface of the handle. The actuating and locking members can be positioned on opposite sides of the handle so that one can be operated with the thumb, and the other one with a finger. Both the actuating and locking members can be moved simultaneously or at different times. This provides the physician with an ability to readily deliver energy from the electrode to a collagen tissue site, and move the electrode in conformance with the geometry of the collagen tissue site.

The handle design provides physician control of the movement of the electrode to closely approximate a desired collagen tissue site. This is readily achieved with the use of only one hand.

DETAILED DESCRIPTION

Figure 1:
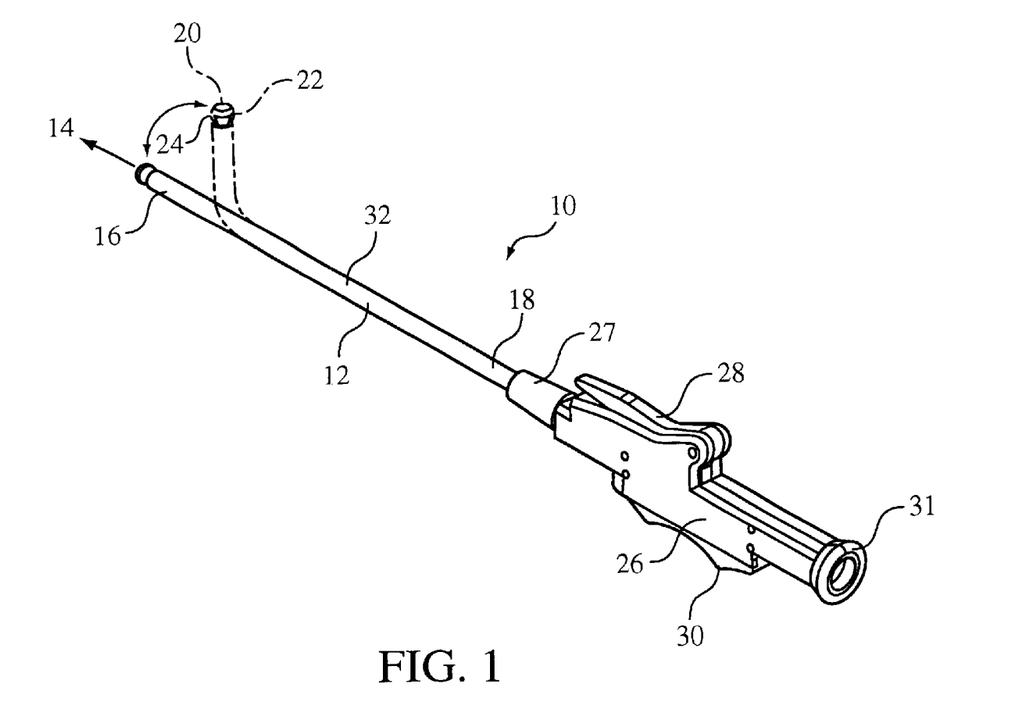
FIG. 1 is a perspective view of the orthopedic apparatus of the present invention including the handle, trocar with deflected distal end, and electrode.

Referring now to FIG. 1, an orthopedic apparatus for effecting a change in collagen tissue in orthopedics, including but not limited to ligaments, joint capsules and connective tissue includes a handpiece 10. The orthopedic apparatus provides for the controlled contraction of collagen fibers, without substantially breaking down or dissociating the collagen fibers, or denature the collagen. The orthopedic apparatus of the present invention is used for controlled contraction of collagen soft tissue of a joint capsule, to treat herniated discs, the meniscus of the knee, for dermatology, to name just a few applications. Energy is delivered from an electrode to a collagen tissue site. The orthopedic apparatus provides a means for moving the electrode in conformance with the geometry of the collagen tissue site. A handle design of the orthopedic apparatus provides physician control of the movement of the electrode to closely approximate a desired collagen tissue site. This is readily achieved with the use of only one hand.

Handpiece 10 includes a trocar 12 with an elongated body and a longitudinal axis 14. A trocar distal end 16 is laterally deflectable about longitudinal axis 14. Trocar 12 also includes a proximal end 20. In one embodiment, trocar has a 9F outer diameter.

An electrode 20 is positioned at trocar distal end 16. In one embodiment, electrode 20 has an outer diameter of 13F. Electrode 20 is capable of delivering substantially uniform energy across an energy delivery surface 22 to an area of collagen fibers. This results in controlled contraction of the collagen fibers while minimizing their dissociation or breakdown. The collagen structure is not denatured and is not ablated. Instead, the collagen structure is contracted. In the case of a joint capsule, the collagen tissue is contracted in order to pull the joint together. If there is too much contraction, then the joint can be physically worked until the collagen fibers stretch to a desired level. Controlled contraction of the collagen tissue is possible because of the design of electrode 20, and the general design of handpiece 10. Electrode 20 is radiused with no sharp edges. Sharp edges introduce hot spots in adjacent tissue which lead to tissue ablation instead of collagen shrinkage.

Electrode 20 has a backside 24 that can be covered with an insulating layer. Use of the insulating layer permits the physician to more accurately control delivery of energy to collagen tissue. In many orthopedic procedures electrode 20 must be moved back and forth, in a painting manner, along the collagen tissue surface. Often, the backside 24 of electrode 20 is adjacent to tissue which is not treated. Therefore, in order to reduce the possibility of ablating the tissue which should not be treated, it is beneficial to provide backside 24 with a layer of insulation so that energy is not delivered from backside 24. The inclusion of an insulating layer to backside 24 can also provide electrode 20 with radiused edges. This is achieved by physically eliminating sharp edges on electrode 20.

Handpiece 10 also includes a handle 26 attached at proximal end 18. A coupler 27 can be included to couple handle 26 to trocar 12. Trocar 12 can extend into an interior of handle 26. Handle 26 includes an actuating member 28 and a locking member 30. The positions of actuating and locking members 28 and 30 can vary. However, it is preferred that actuating member 28 and locking member 30 be positioned on an exterior surface of handle 26 on opposing sides. The physician can then use one hand; the thumb for one and a finger for the other. This provides physician control of trocar distal end 16 and electrode 20 so that collagen tissue is not ablated. Instead it is contracted to a desired state. Actuating member 28 is generally an elongated structure which is pivotally mounted to handle 26. The physician pulls on the end of actuating member that opposes the end which is mounted to handle 26. Actuating member 28 has a resting position when it is closest to handle 26. As actuating member 28 is pulled away from the resting position it moves to one or more activation positions cause trocar distal end 16 to become deflected (articulated). The more actuating member 28 moves away from its resting position, the more trocar distal end 16 is deflected.

Locking member 30 also has a resting position, and a locking position that locks deflected trocar distal end 16 in place. Locking member 30 is releasable from its locking position to its resting position, or to an intermediate position, and holds the activation position of actuating member 28 when the deflection of trocar distal end 16 is adjusted. Handle 26, with associated actuating member 28 and locking member 30, is particularly suitable for use with one hand to easily adjust the amount of deflection of trocar distal end 16.

Actuating member 28 can be directly coupled or indirectly coupled to trocar 12. The same is true with locking member 30. Positioned at a proximal end of handle 16 is a cable connector 31.

As mentioned, in order to avoid the creation of hot spots, electrode 20 has radiused edges, with no square edges. A shrink tube 32 surrounds trocar 12, leaving electrode 20 exposed.

Figure 2:
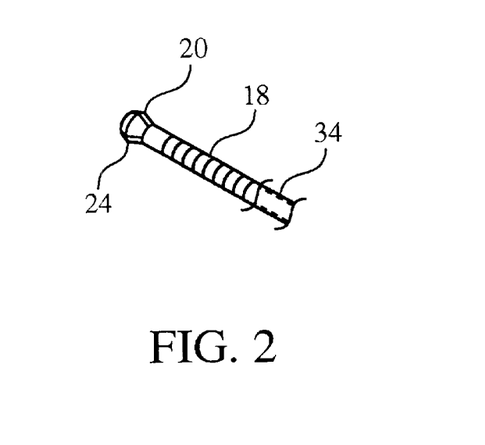
FIG. 2 is a perspective view of the distal end of the trocar, with a layer of insulation partially removed from the distal end.

Referring now to FIG. 2, trocar 12 can be covered and surrounded by an insulation layer 34 which extends to electrode 20. Insulation layer 34 can extend to electrode backside 24. Trocar distal end 16 is laterally deflectable relative to longitudinal axis 14. Deflection can be achieved by a variety of different means including but not limited to segmenting trocar distal end 16, serrating trocar distal end 16, the use of a steering wire (not shown) that extends internally or externally from handle 26 to distal end 16, as well as other methods well known to those skilled in the art. All of trocar 12 may be made of a memory metal or only trocar distal end 16 can be made of a memory metal.

Figure 3:
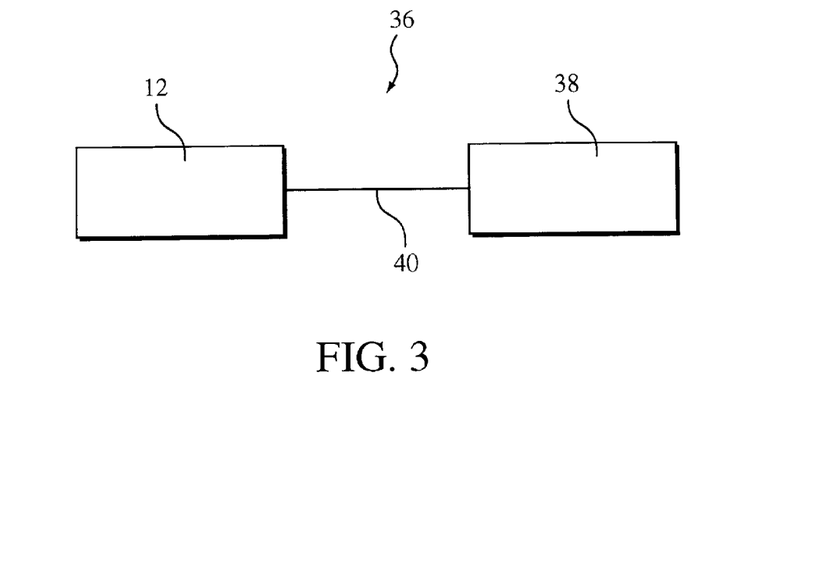
FIG. 3 is a block diagram of the orthopedic apparatus of the present invention illustrating the handpiece, an energy source and a cable connecting the handpiece to the energy source.

As shown in FIG. 3, orthopedic apparatus 36 includes handpiece 12, an energy source 38 and a cable 40 coupled to handpiece 12 and energy source 38. Suitable energy sources include RF, microwave and the like.

Figure 4:
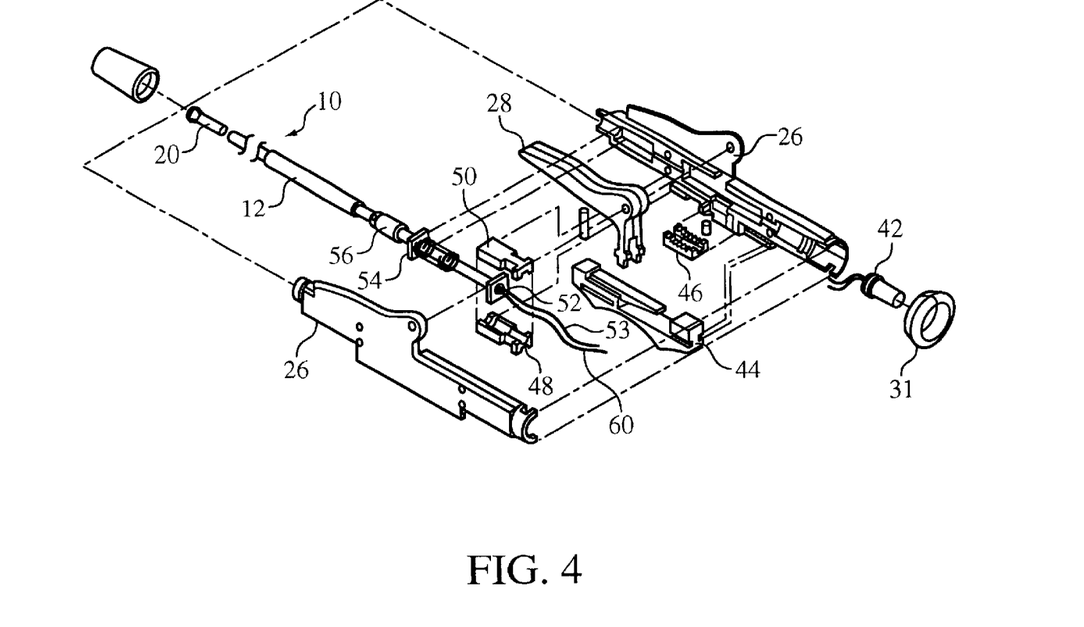
FIG. 4 is an exploded diagram of the orthopedic apparatus of FIG. 1.

Referring now to FIG. 4, an electrical connector 42 is coupled to cable connector 31. Included in handle 26 is a locking slide 44, a locking ratchet 46, a bottom coupler 48, a top coupler 50, a first washer 52 (0.250), a second washer 54 (0.306), an adjustment screw 56, a thermal couple wire 58 and an RF or microwave wire 60. Springs (not shown) permit actuating member 28 to quickly return to a non-deflected state.

Figure 5:
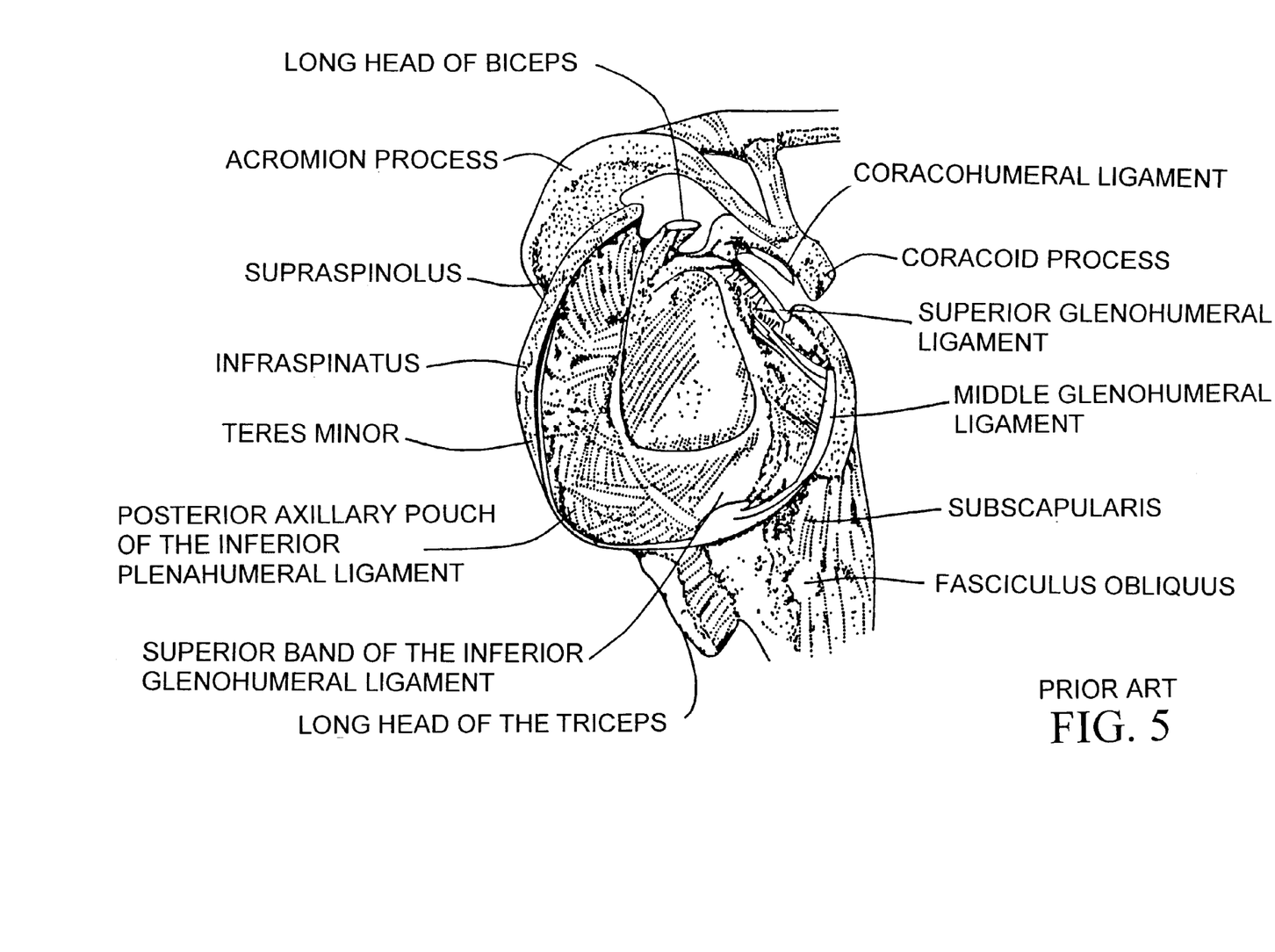
FIG. 5 is a drawing of the right gleno-humeral complex.
Figure 6:
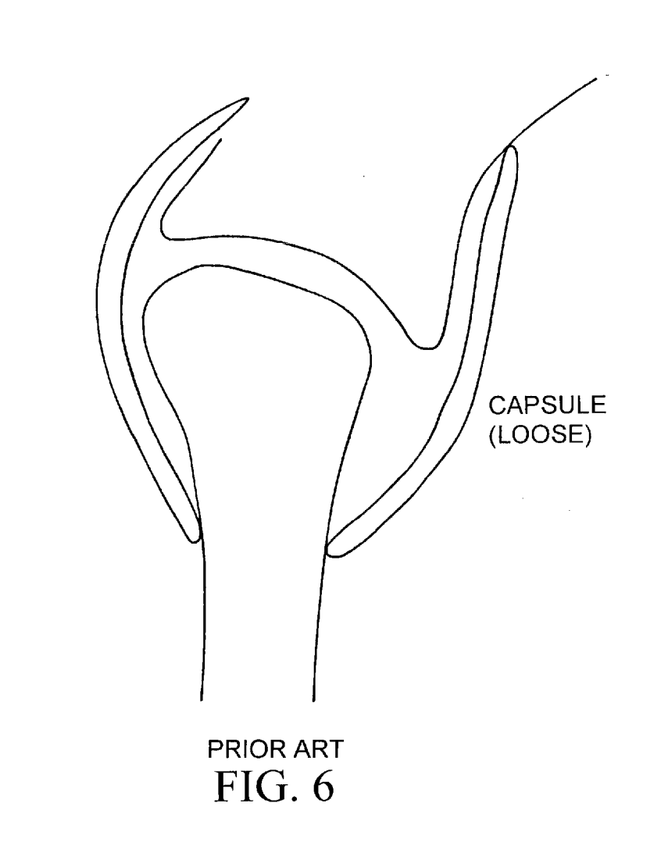
FIG. 6 is a drawing of a loose joint capsule.
Figure 7:
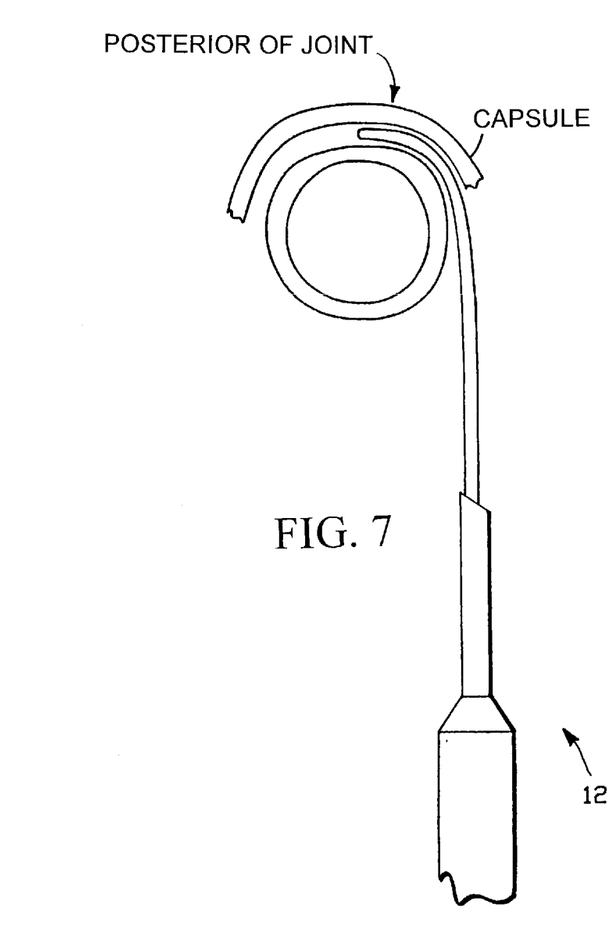
FIG. 7 is a schematic drawing of the apparatus of the invention supplying energy to a joint structure.

In one specific embodiment of the invention, joint capsules are treated to eliminate capsule redundance. More specifically, orthopedic apparatus 36 is used to contract soft collagen tissue in the gleno-humoral joint capsule of the shoulder (FIGS. 5, 6 and 7). When applied to the shoulder, there is a capsular shrinkage of the gleno-humoral joint capsule of the shoulder, and a consequent contracture of the volume, the interior circumference, of the shoulder capsule to correct for recurrent instability symptoms. The degree of capsular shrinkage is determined by the operating surgeon, based on the severity of preoperative symptoms and the condition of the capsule at the time of arthroscopic inspection. The maximum amount of collagen contraction achieved is approximately two-thirds of its original structure.

Handpiece 2 includes trocar 12 that is deflectable but it is also spring loaded. This permits handpiece 12 to be introduced into the shoulder in a straight position, percutaneously or non-percutaneously. The physician begins working and begins to deflect trocar 12 in order to reach a selected tissue site. There may be a series of deflection steps needed in order to reach the tissue site and begin apply energy to the collagen tissue. The trocar is deflected to a first position, then to a second, perhaps back to the first position and to a non-deflected position, and electrode 20 is painted back and forth, up and down a collagen tissue site. Articulating and locking members 28 and 30, and electrode 20 with radiused edges, permits the controlled delivery energy in order to contract the collagen tissue and not ablate the tissue. Articulating and locking members 28 and 30 provide the physician with sufficient control to vary the position of electrode 20 in both difficult and easy access areas, in order to provide controlled delivery of energy to contract collagen tissue and minimize ablation. Without articulating and locking members 28 and 30 there is insufficient control of energy delivery to provide controlled ablation. The combination of the two provides a ratcheting effect and free articulation and movement of electrode 20 along a desired collagen tissue surface.

Figure 8:
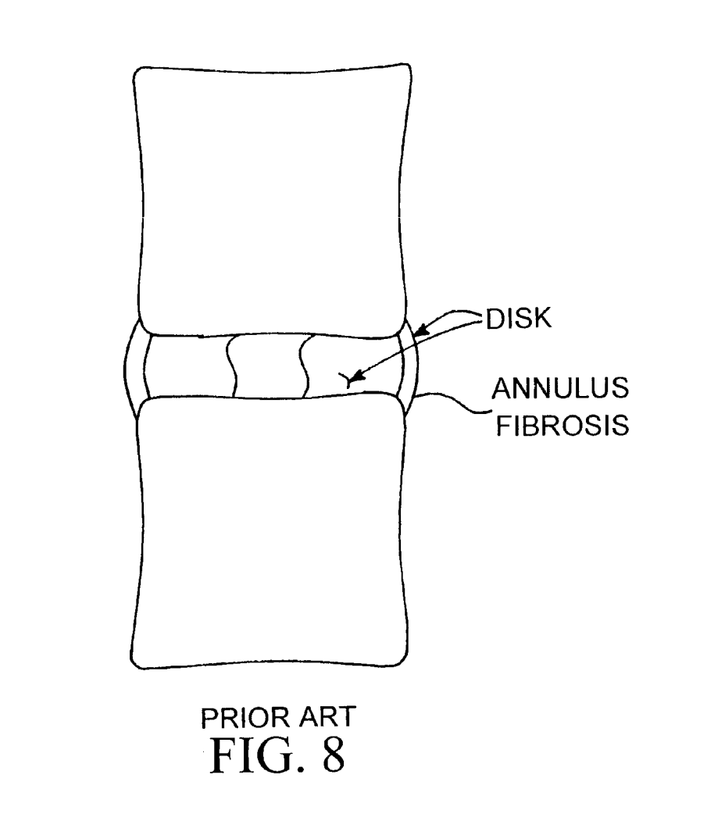
FIG. 8 is a sectional view of a disc positioned between two vertebrae.
Figure 9:
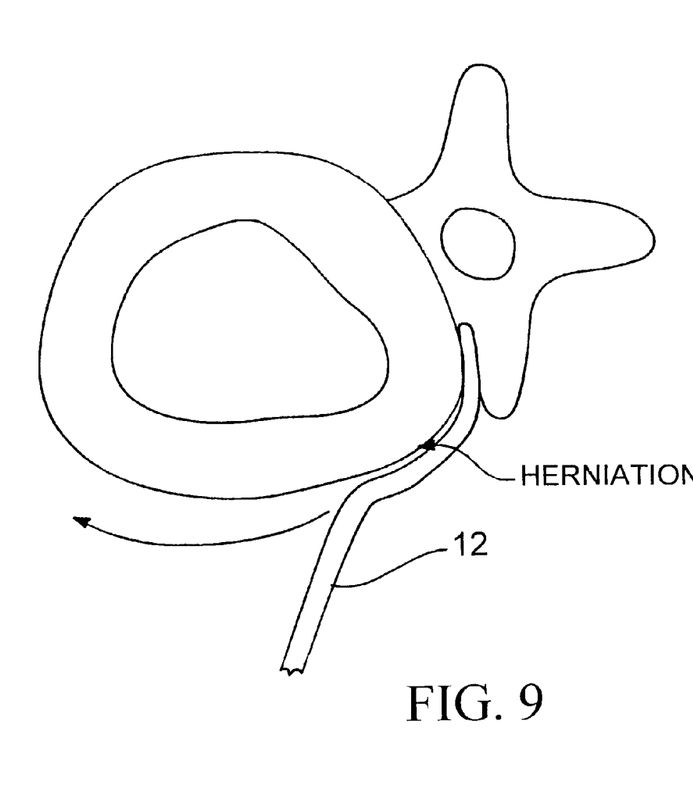
FIG. 9 is a schematic diagram of the apparatus of the invention with an electrode supplying energy to a herniated disc.

FIGS. 8 and 9 illustrated use of handpiece 10 with discs of the spine.

Handpiece 10 provides RF and microwave energy to collagen tissue in temperature ranges of about 43 to 90 degrees C, 43 to 75 degrees C and 45 to 60 degrees C.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. An orthopedic apparatus, comprising:
    a trocar including a trocar elongated body with a trocar longitudinal axis, a trocar distal end that is laterally deflectable relative to the trocar longitudinal axis, and a trocar proximal end;
    an electrode positioned at the trocar distal end, the electrode delivering substantially uniform energy across an energy delivery surface of the electrode to an area of collagen fibers adjacent to the energy delivery surface to cause a controlled amount of contraction of the collagen fibers while minimizing dissociation and breakdown of the collagen fibers; and
    a handle positioned at a proximal end of the orthopedic device from which the trocar distally extends, the handle including an actuating member and a locking member positioned on opposing sides of the handle, the actuating member having a resting position and one or more activation positions that are defined by a locking ratchet in the handle which defines a plurality of discrete steps for the actuating member, the actuating member being operably attached to the trocar such that activation of the actuating member causes the trocar distal end to ratchet in a series of lateral deflection steps as controlled by the discrete steps of the locking ratchet, the locking member having resting position and a locking position that locks the deflected trocar distal end in place, the locking member being releasable from the locking position to the resting position or to an intermediate position to hold the activation position of the actuating member and change the deflection of the trocar distal end, wherein the actuating member and the locking member are configured to be each operable by a thumb and a finger of a single hand which holds the handle.

2. The orthopedic apparatus of claim 1, wherein the electrode has radiused edges.

3. The orthopedic apparatus of claim 1, wherein the electrode has no square edges.

4. The orthopedic apparatus of claim 1, further comprising:
    an insulating layer positioned around an exterior of the trocar that does not cover the energy delivery surface of the electrode.

5. The orthopedic apparatus of claim 1, further comprising:
    a non-conductive layer positioned on an opposite side of the electrode from the energy delivery surface of the electrode.

6. The orthopedic apparatus of claim 1, further comprising:
    a shrink tube surrounding the trocar that does not cover the energy delivery surface of the electrode.

7. The orthopedic apparatus of claim 1, wherein the distal end of the trocar is serrated.

8. The orthopedic apparatus of claim 1, wherein the distal end of the trocar is made of a memory metal.

9. The orthopedic apparatus of claim 1, wherein the trocar is made of a memory metal.

10. The orthopedic apparatus of claim 1, wherein the trocar extends into an interior of the handle.

11. The orthopedic apparatus of claim 1, wherein the actuating member pivots in a lateral direction relative to a longitudinal axis of the handle.

12. The orthopedic apparatus of claim 1, wherein the locking member is slideably positioned on an exterior surface of the handle.

13. The orthopedic apparatus of claim 1, further comprising:
    a coupler positioned at the trocar proximal end.

14. The orthopedic apparatus of claim 1, further comprising:
    a cable connector positioned at a proximal end of the handle.

15. The orthopedic apparatus of claim 1, wherein the electrode is an RF electrode.

16. The orthopedic apparatus of claim 1, wherein the electrode is a microwave electrode.

17. An orthopedic apparatus, comprising:
    a trocar including a trocar elongated body with a trocar longitudinal axis, a trocar distal end that is laterally deflectable relative to the trocar longitudinal axis, and a trocar proximal end;

an RF electrode positioned at the trocar distal end, the electrode delivering substantially uniform energy across an energy delivery surface of the electrode to an area of collagen fibers adjacent to the energy delivery surface to cause a controlled amount of contraction of the collagen fibers while minimizing dissociation and breakdown of the collagen fibers; and a handle positioned at a proximal end of the orthopedic device from which the trocar distally extends, the handle including an actuating member and a locking member positioned on opposing sides of the handle, the actuating member having a resting position and one or more activation positions that are defined by a locking ratchet in the handle which defines a plurality of discrete steps for the actuating member, the actuating member being operably attached to the trocar such that activation of the actuating member causes the trocar distal end to ratchet in a series of lateral deflection steps as controlled by the discrete steps of the locking ratchet, the locking member having a resting position and a locking position that locks the deflected trocar distal end in place, the locking member being releasable from the locking position to the resting position or to an intermediate position to hold the activation position of the actuating member and change the deflection of the trocar distal end, wherein the actuating member and the locking member are configured to be each operable by a thumb and a finger of a single hand which holds the handle;

an RF energy source; and a cable to connect the RF energy source to the handle and the electrode.

18. An orthopedic apparatus, comprising:

a trocar including a trocar elongated body with a trocar longitudinal axis, a trocar distal end that is laterally deflectable relative to the trocar longitudinal axis and a trocar proximal end;

a microwave electrode positioned at the trocar distal end, the electrode delivering substantially uniform energy across an energy delivery surface of the electrode to an area of collagen fibers adjacent to the energy delivery surface to cause a controlled amount of contraction of the collagen fibers while minimizing dissociation and breakdown of the collagen fibers; and a handle positioned at a proximal end of the orthopedic device from which the trocar distally extends, the handle including an actuating member and a locking member positioned on opposing sides of the handle, the actuating member having a resting position and one or more activation positions that are defined by a locking ratchet in the handle which defines a plurality of discrete steps for the actuating member, the actuating member being operably attached to the trocar such that activation of the actuating member causes the trocar distal end to ratchet in a series of lateral deflection steps as controlled by the discrete steps of the locking ratchet, the locking member having a resting position and a locking position that locks the deflected trocar distal end in place, the locking member being releasable from the locking position to the resting position or to an intermediate position to hold the activation position of the actuating member and change the deflection of the trocar distal end, wherein the actuating member and the locking member are configured to be each operable by a thumb and a finger of a single hand which holds the handle;

a microwave energy source; and a cable to connect the microwave energy source to the handle and the electrode.

* * * * *

UNITED STATES PATENT AND TRADEMARK OFFICE
CERTIFICATE OF CORRECTION

| | |
|---|---|
| PATENT NO. | : 6,461,353 B1 |
| APPLICATION NO. | : 08/888359 |
| DATED | : October 8, 2002 |
| INVENTOR(S) | : James A. Baker Jr., Edward J. Gough and Gary S. Fanton |

It is certified that error appears in the above-identified patent and that said Letters Patent is hereby corrected as shown below:

Cover page, change item (75) to read as follows:

(75) Inventors: James A. Baker, Jr., Palo Alto; Edward J. Gough, Menlo Park; Gary S. Fanton, Portola Valley, all of CA (US)

In the U.S. Documents, page 2:

U.S. Patent 5,810,809: replace "9/1998" with --8/1998--.

In Foreign Patent Documents:

EP Patent 0 521 595: replace "7/1993" with --1/1993--.

In the specification and claims:

Column 5, line 19: replace "denature" with --denaturing--.

Column 7, line 14: replace "2" with --10--.

Column 7, line 15: replace "12" with --10--.

Claim 1, column 8, line 9: after "having", insert --a--.

Signed and Sealed this

Twentieth Day of February, 2007

JON W. DUDAS
*Director of the United States Patent and Trademark Office*